United States Patent
Ritchie et al.

(10) Patent No.: US 6,371,503 B2
(45) Date of Patent: *Apr. 16, 2002

(54) WHEELCHAIR AUTOMATIC ANTI-ROLLBACK ASSEMBLY

(75) Inventors: James K. Ritchie, Waterford, CT (US); James A. Marquis, Springfield, MA (US)

(73) Assignee: 210 Innovations LLC, Waterford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/910,737

(22) Filed: Jul. 24, 2001

Related U.S. Application Data (63) Continuation of application No. 09/578,488, filed on May 26, 2000, now Pat. No. 6,279,936, which is a continuation of application No. 09/026,902, filed on Feb. 20, 1998, now Pat. No. 6,092,824.
(60) Provisional application No. 60/039,485, filed on Feb. 28, 1997, now abandoned.

(51) Int. Cl.[7] ................................................. B62M 1/14
(52) U.S. Cl. ............................... 280/304.1; 280/250.1; 188/2 F
(58) Field of Search .......................... 280/304.1, 250.1; 188/2 F, 68; D12/131, 133; 297/DIG. 4

(56) References Cited

U.S. PATENT DOCUMENTS

| | | | |
|---|---|---|---|
| 2,259,924 A | | 10/1941 | Connolly |
| 2,753,919 A | | 7/1956 | Sill |
| 3,302,757 A | * | 2/1967 | Eagleson, Jr. et al. |
| 3,529,700 A | * | 9/1970 | Marshall |
| 3,903,513 A | * | 9/1975 | Green et al. ................ 340/278 |
| 4,320,818 A | | 3/1982 | Knoche |
| 4,476,964 A | | 10/1984 | Broman |
| 4,538,825 A | * | 9/1985 | Delahoussaye et al. ...... 280/242 WC |
| 4,560,033 A | * | 12/1985 | DeWoody et al. ........... 188/2 F |
| 4,565,385 A | | 1/1986 | Morford |
| 4,623,043 A | * | 11/1986 | Babilas ........................ 188/2 F |
| 4,691,933 A | | 9/1987 | Strauss |
| 4,877,260 A | | 10/1989 | Howland |
| 4,887,830 A | * | 12/1989 | Fought et al. ............ 280/304.1 |
| 5,137,295 A | | 8/1992 | Peek |
| 5,197,750 A | * | 3/1993 | DiGeorge ................. 280/250.1 |
| 5,203,433 A | * | 4/1993 | Dugas ......................... 188/2 F |
| 5,232,236 A | | 8/1993 | Korpi |
| 5,358,266 A | | 10/1994 | Roth et al. |
| 5,577,748 A | | 11/1996 | Dombrowski et al. |
| 5,984,334 A | | 11/1999 | Dugas |

FOREIGN PATENT DOCUMENTS

| | | |
|---|---|---|
| WO | 90/14064 | 11/1990 |
| WO | 90/14065 | 11/1990 |

* cited by examiner

Primary Examiner—Avraham H. Lerner
(74) Attorney, Agent, or Firm—Pillsbury Winthrop LLP (57) ABSTRACT

An anti-rollback assembly adapted or adaptable for use in combination with a wheelchair. The anti-rollback assembly includes a one-way brake assembly automatically immobilizing the wheelchair against rearward movement when the occupant attempts to rise from or sit in a seat member of the wheelchair, yet at the same time does not prevent the wheelchair from moving in a forward direction. Conversely, when the occupant is fully seated in the seat member, the one-way brake assembly is disengaged so that the wheelchair can move freely in forward or rearward directions. The assembly can be retrofitted onto existing wheelchairs, and is adjustable to fit various size wheelchairs.

29 Claims, 7 Drawing Sheets

WHEELCHAIR AUTOMATIC ANTI-ROLLBACK ASSEMBLY

The present application is a continuation of and claims priority to U.S. patent application Ser. No. 09/578,488, filed May 26, 2000, now U.S. Pat. No. 6,279,936, which is a continuation of and claims priority to U.S. patent application Ser. No. 09/026,902, filed Feb. 20, 1998, now U.S. Pat. No. 6,092,824, which in turn claims priority to U.S. Provisional Application No. 60/039,485, filed Feb. 28, 1997, now abandoned.

BACKGROUND OF THE INVENTION

1. Field of the Invention

The present invention relates generally to wheelchairs and more particularly to an anti-rollback assembly that operatively associates with a wheelchair to prevent the wheelchair from rolling backwards and away from its occupant as the occupant attempts to mount or dismount the wheelchair, yet permits the wheelchair in an unoccupied state to be moved in a forward direction.

The anti-rollback assembly of the present invention is especially suitable for wheelchairs of invalids, the cognitively impaired, the elderly, and sufferers of physically and mentally disabling diseases such as Alzheimer's.

2. Description of the Related Art

Almost all wheelchairs possess a parking brake in one form or another which, when actuated, maintains the wheelchair in a stationary position by preventing one or both of the large drive wheels of the wheelchair from rotating about a common central axis. Perhaps the most crucial periods for the wheelchair to remain stationary are when a person attempts to sit down in and occupy the wheelchair and when the occupant attempts to stand up from and vacate the wheelchair. The natural motion of a person performing these acts imparts a force in the rearward direction on the wheelchair, which, without the benefit of an actuated parking brake, causes the wheelchair to move backwards and away from the person.

As a consequence of the mental and physical infirmities suffered by many wheelchair occupants, especially patients suffering from Alzheimer's disease and other mental frailties, occupants often forget to actuate manually-operated parking brakes prior to attempting to rise from the wheelchair, or neglect to inspect the parking brake to ensure it is engaged in a locked position prior to attempting to sit down into the wheelchair. Failure to engage the manually-operated parking brake in its locked position presents a serious hazard of injury to both the occupant and his or her caretaker, since the wheelchair is unimpeded from rolling back and away from the occupant as the occupant attempts to rise from or sit down in the wheelchair.

To address the shortcomings of manually-operated parking brakes, several different automatically-operated locking brake assemblies have been proposed. U.S. Pat. No. 5,203,433 sets forth a discussion of some conventional automatic locking brake assemblies. Each of the conventional assemblies mentioned in U.S. Pat. No. 5,203,433 is characterized by the provision of a locking member that, unless manually disengaged, prevents or at least substantially obstructs both the forward or rearward movement of the wheelchair with which the assembly is associated when the wheelchair is unoccupied.

However, one of the most important functions served by an automatic wheelchair brake is that it not only prevent the wheelchair from rolling backwards and away from its occupant as the occupant mounts or dismounts the wheelchair, but that the brake also not substantially obstruct the forward motion of the wheelchair when unoccupied so that the unoccupied wheelchair can be easily maneuvered to a desirable location for use or temporary storage.

A long-felt need therefore exists to provide an automatically-operated anti-rollback assembly for a wheelchair that biases a braking mechanism into an activated position when the wheelchair is unoccupied to prevent the wheelchair from rolling back when it is mounted or dismounted in normal operation, yet, while in the activated position, permits the forward motion of the unoccupied wheelchair.

SUMMARY OF THE INVENTION

It is, therefore, an object of the present invention to provide an anti-rollback assembly that solves the aforementioned problems associated with the related art as well as other problems and addresses the long-felt need outlined above.

It is another object of the present invention to provide an automatic anti-rollback assembly which is reliable in operation, easy to use, and economical to manufacture.

A further object of the present invention is to provide an automatic anti-rollback assembly that can be easily and inexpensively retrofitted to existing wheelchairs.

It is another object of the present invention to provide an automatic anti-rollback assembly that, when operatively associated with a wheelchair, permits the unoccupied wheelchair to freely roll in a forward direction, yet impedes only the rearward motion of the wheelchair, so that the unoccupied wheelchair can be used, for example, as a walker.

Still another object of the present invention is the provision of a wheelchair having an automatic anti-rollback assembly with an ambulation monitor which activates an alarm when the wheelchair occupant attempts to vacate the wheelchair.

In accordance with the principles of the present invention, these and other objects are attained by the provision of an automatic anti-rollback assembly that is adapted or adaptable for use in combination with a wheelchair. The automatic anti-rollback assembly generally comprises a one-way brake assembly supportable on a frame structure of a wheelchair, biasing member, and a brake releasing assembly. The one-way brake assembly includes a one-way brake member (or brake arm). When used in combination with a wheelchair, the one-way brake assembly is movable between a non-activated position in which the one-way brake member is positioned to permit the rear drive wheel assembly to rotate in forward and rearward directions to enable the wheelchair to move freely in both the forward and rearward directions, and an activated position in which the one-way brake member is positioned to prevent rotation of the rear drive wheel assembly in the rearward direction so as to prevent movement of the wheelchair in the rearward direction, yet continues to permit rotation of the rear drive wheel assembly in the forward direction for forward movement of the wheelchair. The biasing member serves to impart a biasing force to urge the one-way brake assembly towards the activated position. The brake releasing assembly is operatively associated with the one-way brake assembly and the biasing member, and is movable in response to the wheelchair being occupied to overcome the biasing force of the biasing member so as to move the one-way brake assembly from the activated position to the non-activated position, thereby enabling the wheelchair to freely move in both the forward and rearward directions unencumbered by the one-way brake member.

In accordance with the present invention, the occupant of the wheelchair is not required to set a conventional parking brake. Instead, the wheelchair is automatically immobilized against backward movement by the anti-rollback device when the occupant is attempting to rise from or sit himself in the seat member. In addition, when the occupant is fully seated in the seat member, the anti-rollback device is disengaged, i.e., the one-way brake assembly is moved into a non-activated position, so that the wheelchair can be freely moved forward or backwards unencumbered by the one-way brake member.

These and other objects, features, and advantages of the present invention will become apparent from the following detailed description when taken in conjunction with the accompanying drawings which illustrate, by way of example, the principles of the present invention.

BRIEF DESCRIPTION OF THE DRAWINGS

The accompanying drawings illustrate an embodiment of the present invention. In such drawings.

DESCRIPTION OF THE PREFERRED EMBODIMENTS

A detailed description of a conventional wheelchair structure will be discussed hereinbelow for the purposes of assisting in the detailed description of the anti-rollback assembly of the present invention and explaining the manner in which the anti-rollback assembly is operatively supported on a wheelchair. It is understood, however, the present invention is not restricted to the illustrated wheelchair or the construction and arrangement of the individual components of the illustrated wheelchair.

Figure 1:
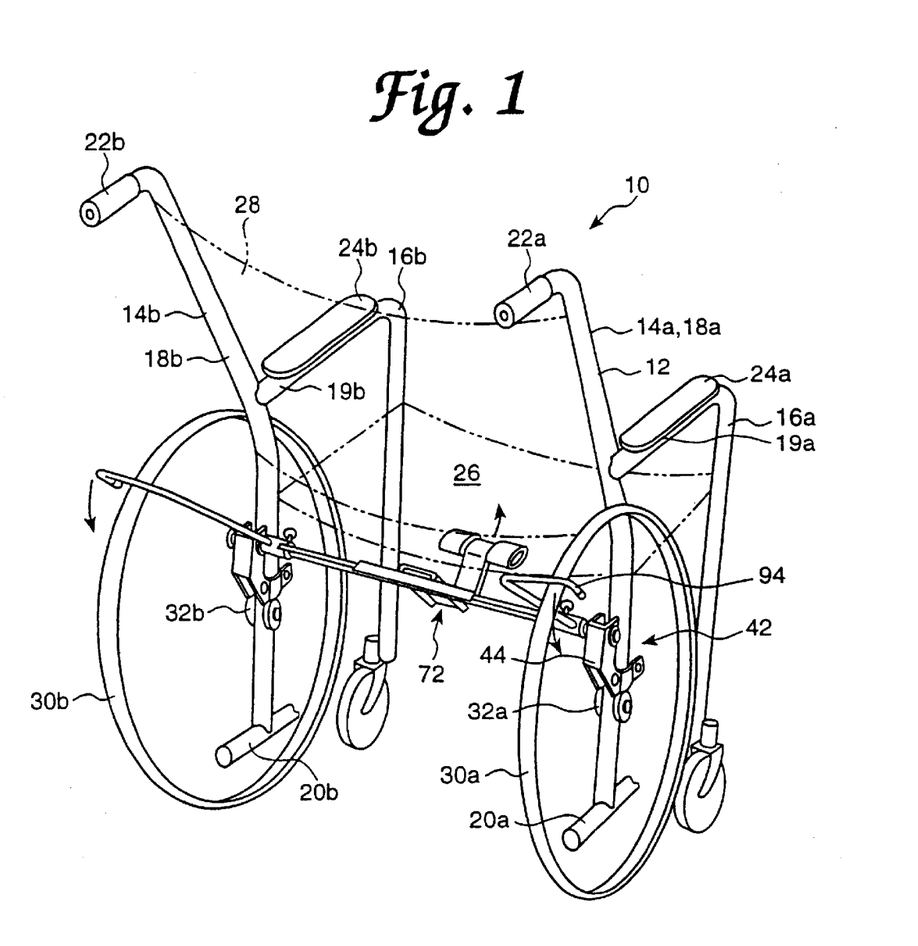
FIG. 1 is a perspective rear view of a wheelchair including an anti-rollback assembly in accordance with a preferred embodiment of the present invention, in which the range of movement of the anti-rollback assembly between non-activated and activated positions is depicted by arrows.
Figure 2A:
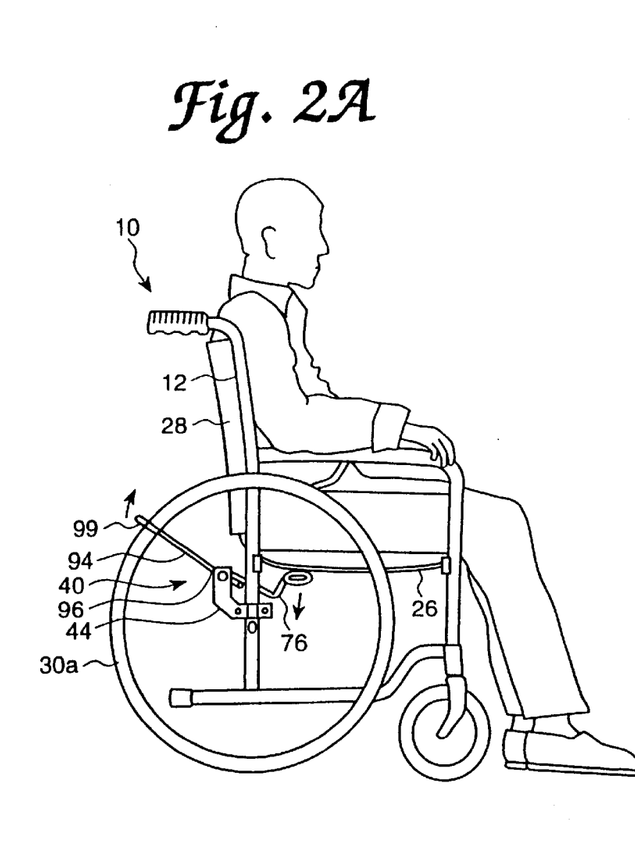
FIGS. 2A and 2B are side elevational views of the wheelchair of FIG. 1 in occupied and unoccupied states, respectively.
Figure 2B:
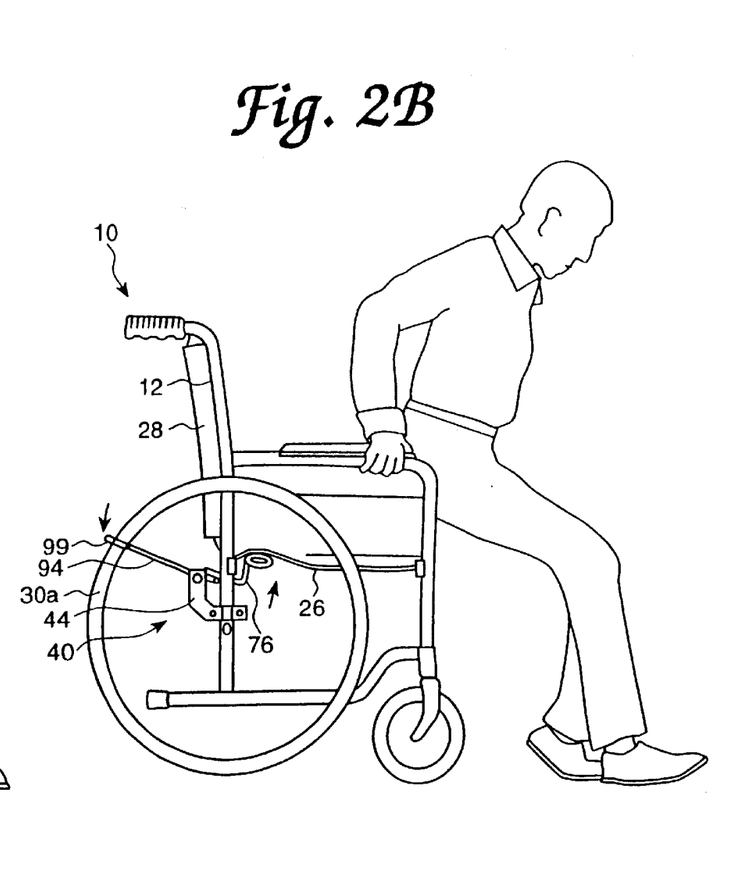

Referring now to the drawings, there is shown in FIGS. 1, 2A, and 2B a wheelchair generally is designated by reference numeral 10. The wheelchair 10 includes a frame structure 12 comprising a pair of opposing side frames 14a and 14b laterally spaced from and substantially parallel with one another. The opposing side 20 frames 14a and 14b have respective front upright members 16a and 16b and respective rear upright members 18a and 18b. In the illustrated embodiment, the front upright member 16a and the rear upright member 18a of the side frame 14a 25 include longitudinal axes oriented substantially vertical, and are interconnected with crossbars 19a and 20a. The front upright member 16b and the rear upright member 18b of the other side frame 14b are arranged and interconnected in a similar manner with crossbars 19b and 20b. Handles 22a and 22b are fitted onto upper ends (unnumbered) of the rear upright members 18a and 18b, respectively. Arm rests 24a and 24b are secured to upper surfaces of the crossbars 19a and 19b, respectively.

The wheelchair 10 further includes a flexible seat member 26 extending between the opposing side frames 14a and 14b and arranged in a substantially horizontal orientation so as to permit an occupant to sit thereon. A flexible back support member 28 extends between the rear upright members 18a and 18b and, together with the seat member 26, define a seating area (unnumbered) for supporting the wheelchair occupant.

As shown in FIG. 1., the wheelchair 10 further includes rear drive wheel assemblies comprising two large rear drive wheels 30a and 30b which are manually rotatable by the occupant to rotate about hubs 32a and 32b, respectively. The hubs 32a and 32b are respectively attached to the rear upright members 18a and 18b with axle bolts (unnumbered) and each include a plurality of spokes (not shown) extending therefrom to interconnect the hubs 32a and 32b to their respective drive wheels 30a and 30b. Front wheel assemblies comprise small wheels 34a and 34b swivably connected to the front upright members 16a and 16b, respectively, to facilitate turning of the wheelchair 10.

Although not shown, it is understood that in accordance with the present invention, the wheelchair 10 can include additional components, such as footrests. It is further understood that in accordance with the present invention the wheelchair can omit one or more of the components discussed above and illustrated in the drawings, so long as the wheelchair is characterized as being capable of operatively supporting the anti-rollback feature of the present invention.

One embodiment of the automatic anti-rollback assembly of the present invention, which is generally designated by reference numeral 40, will now be described with greater specificity hereinbelow.

Figure 3:
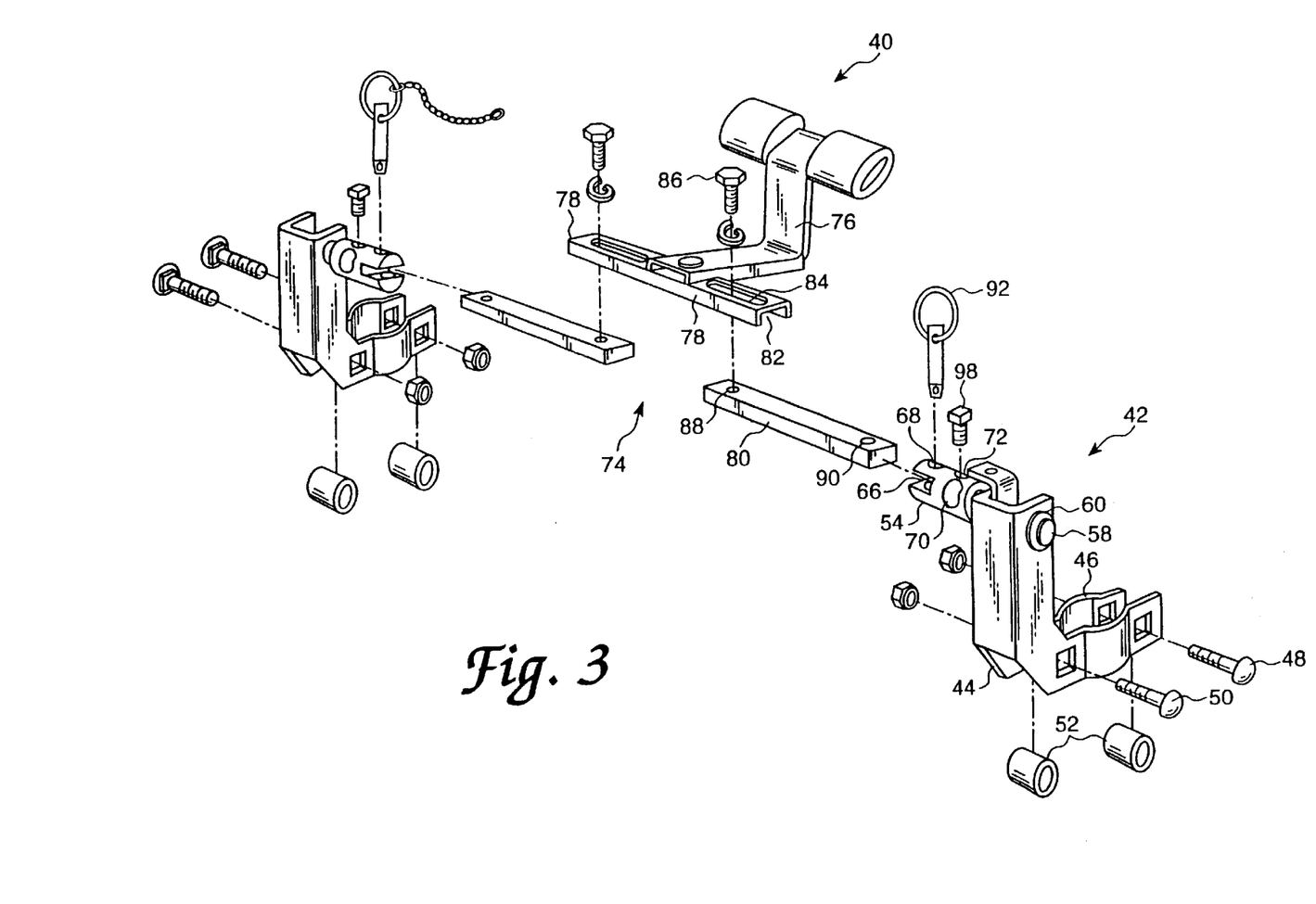
FIG. 3 is an exploded view of mounting and brake releasing assemblies of the anti-rollback assembly of FIG. 1.
Figure 4:
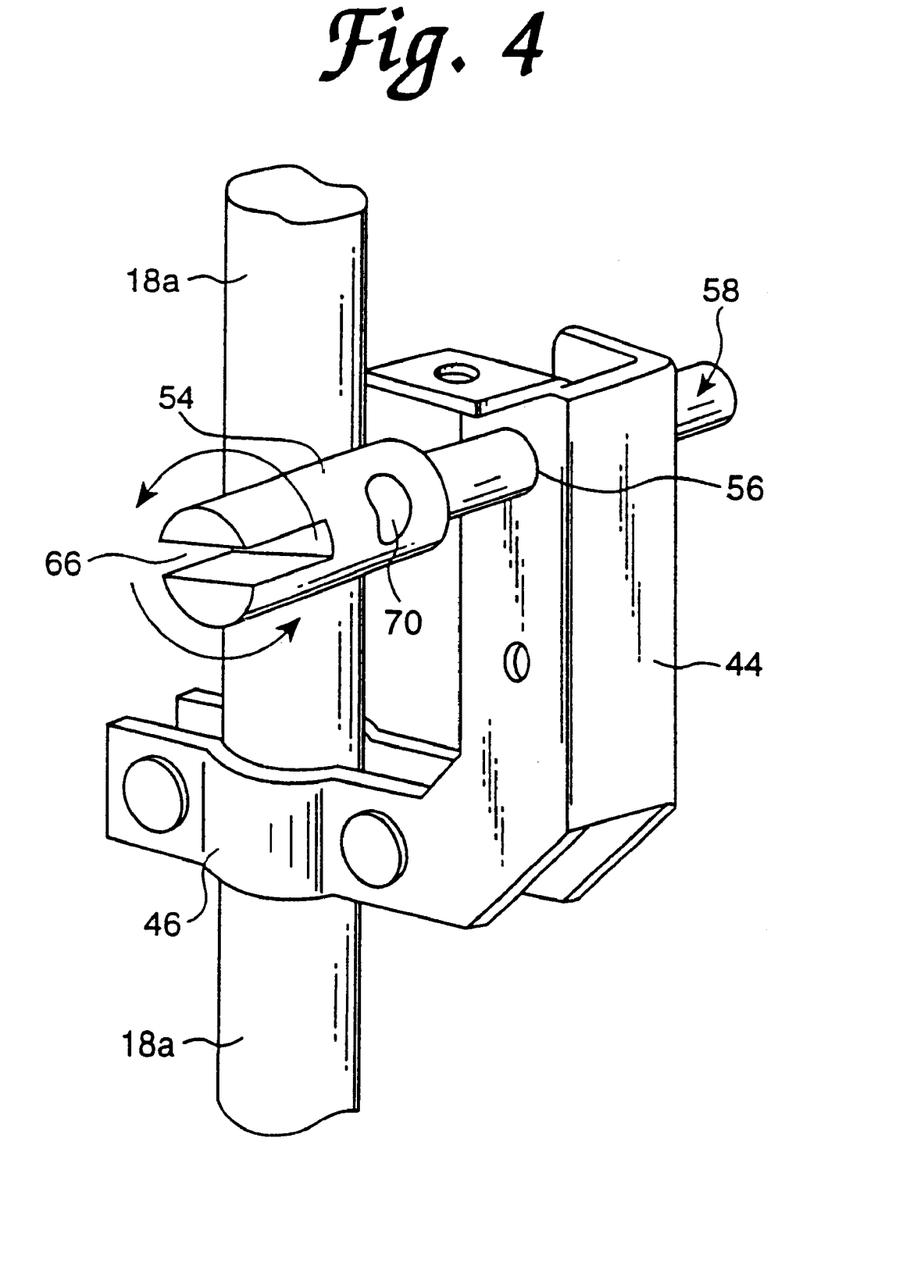
FIG. 4 is a perspective view of a bracket and brake arm supporting member of the mounting assembly of FIGS. 1 and 3.

Referring to FIGS. 3 and 4, the illustrated automatic anti-rollback assembly 40 includes two mounting assemblies. For explanatory purposes, only one of the two mounting assemblies, which is generally designated by reference numeral 42, will be described below.

The mounting assembly 42 includes a mounting bracket 44 with a discontinuous circular clamping end 46, which accommodates the rear upright member 18a. Nut-bolt combinations 48 and 50 serve to secure the mounting bracket 44 to the rear upright member 18a. Reinforcement spacers 52 may be used in combination with the nut-bolt combinations 48 and 50 to prevent bowing of the bolts. The reinforcement spacers 52 can be made of, for example, nylon or other plastics. As shown in FIGS. 1, 2A, and 2B, the clamping end 46 of the mounting bracket 44 is positioned immediately above the axle bolt associated with hub 32a.

Figure 5:
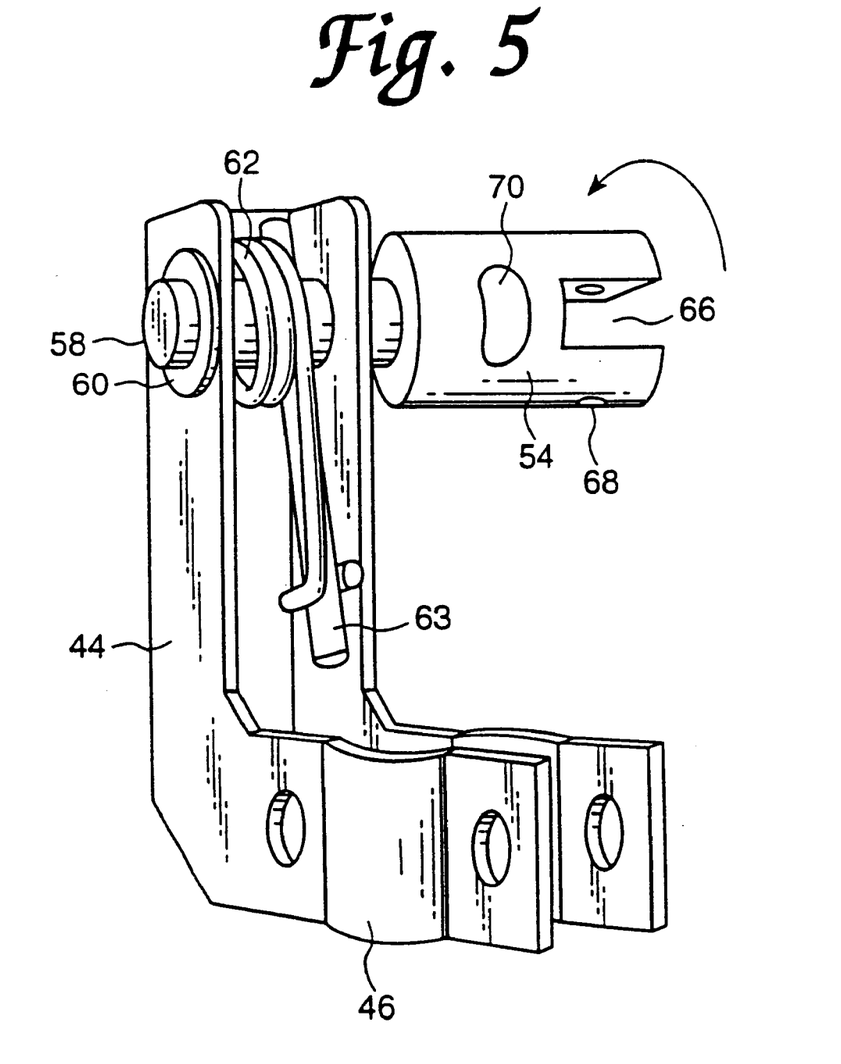
FIG. 5 is a rear view of the bracket of the mounting assembly depicting a biasing member.

The mounting assembly 42 further includes a movable brake-arm supporting member 54 (also referred to as a brake-member supporting member or pivotable collar), which is substantially configured as a clevis yoke. In the illustrated embodiment, the brake-arm supporting member 54 is rotatable about its longitudinal axis between first and second positions. Opposing sides of the mounting bracket 44 define aligned apertures, one of which is designated by reference numeral 56 in FIG. 4. The apertures 56 are sized to receive a shaft 58 co-axially extending from and integral with the pivotable collar 54. The shaft 58 is secured to the mounting bracket 44 with, for example, a lock cap 60. As shown in FIG. 5, a torsion spring 62 is accommodated in the mounting bracket 44 and connected to the shaft 58 of the pivotable collar 54 via pin 63 to urge the pivotable collar 54 into its first position.

The opposite end (unnumbered) of the pivotable collar 54 defines a slot 66 diametrically positioned and axially extending a certain depth into pivotable collar 54. A first bore 68 is diametrically defined within the pivotable collar 54, and arranged orthogonally relative to the slot 66 to intersect the slot 66. Second and third bores 70 and 72 are each diametrically disposed, arranged orthogonally relative to each other to intersect each other, and are interposed between the slot 66 and the shaft 58. The functions of the slot 66 and the first, second, and third bores 68, 70, and 72 will be described below.

Still referring to FIG. 3, the automatic anti-rollback assembly 40 further includes a brake releasing assembly, which is generally designated by reference numeral 74.

The brake releasing assembly 74 includes a substantially L-shaped actuator lever 76, adjustor plate 78, and connector plates 80. For explanatory purposes, the connector plate 80 and the side of the adjustor plate 78 operatively associated with mounting assembly 42 will be described below.

The actuator lever 76 is cantilevered at a central portion (unnumbered) of the adjustor plate 78. The end (unnumbered) of the adjustor plate 78 defines an exposed lateral port 82, which receives a portion of the connector plate 80. The upper region of the adjustor plate 78 has an elongated slot 84 defined therethrough in communication with the lateral port 82. (As shown in FIG. 3, the slots 84 are located on each side of the central portion of the adjustor plate 78.) A nut-washer combination 86 engages a first aperture 88 of the connector plate 80 and the elongated slot 84 to thereby secure the adjustor plate 78 to the connector plate 80. The end of the connector plate 80 opposite to the first aperture 88 defines a second aperture 90.

As shown in FIGS. 2A and 2B, when the brake releasing assembly 74 is connected to the mounting assembly 42, the brake releasing assembly 74 is positioned immediately underneath the seat member 26. The connection of the brake releasing assembly 74 to the mounting assembly 42 will now be described with reference to FIG. 3.

The slot 66 of the pivotable collar 54 receives the end of the adjustor plate 78 containing the second aperture 90 so that the first bore 68 and the second aperture 90 are aligned. A quick-release pin 92 is inserted through the aligned first bore 68 and second aperture 90 to secure the brake releasing assembly 74 to the mounting assembly 42. The provision of the quick-release pin 92 or similar connecting device facilitates the quick and easy separation and removal of the brake releasing assembly 74. When the wheelchair 10 is of the collapsible variety, the frames 14a and 14b and associated wheels on either side of the seat member 26 can thereby be folded together for convenient stowage. The provision of a quick-releasing mechanism to facilitate the ability of the wheelchair 10 to be collapsed and stored represents one of the many advantages of the present invention.

Another of the advantages of the illustrated embodiment rests in the configuration of the elongated slots 84 of the adjustor plate 78, which provides for an adjustable positional relationship with the first aperture 88 of connector plate 80. This feature makes the illustrated anti-rollback assembly 40 adaptable and retrofittable to wheelchairs of various widths. Although not shown, it is noted that the elongated slots 84 can be replaced with, for example, a series of spaced apertures.

The anti-rollback assembly 40 also includes a brake member (or brake arm) 94, a proximal end portion 96 of which is received in the second bore 70 of the pivotable collar 54 and secured thereto with a set screw 98 (FIG. 3). (The brake member 94 and mounting assembly 42 collectively form a one-way brake assembly in this embodiment.) As respectively shown in FIGS. 2A and 2B, a distal end portion 99 of the brake arm 94 either is spaced from a rear region of the drive wheel 30a (when the wheelchair 10 is occupied) or rests on the drive wheel 30a (when the wheelchair 10 is unoccupied or the occupant attempts to rise from or sit down into the wheelchair 10). As is believed evident from this description, the positional relationship-of the brake arm 94 to the pivotable collar 54 can be adjusted (by loosening set screw 98) to make the brake arm 94 adaptable and retrofittable to wheelchairs of various drive wheel sizes.

The operational movement of the anti-rollback assembly 40 will be described below with reference to FIGS. 1, 2A, 2B, and 3.

In its unoccupied state, the torsion spring 62 imparts a biasing force to urge the brake-arm supporting member 54 towards the first position, which in turn urges the seat member 26 towards its upper position and the distal end portion 99 of the brake arm 94 into the activated position. As is seen from the arrows in FIG. 1, 2A and 2B, in the illustrated embodiment the axis of the pivotal collar 54 is located higher and to the rear of the axis of the drive wheels 30a and 30b. As a consequence, the torsion spring 62 applies a biasing force along a non-radial direction relative to the drive wheels 30a and 30b. As shown by the arrows in FIGS. 1, 2A and 2B, this biasing force urges the end portion 99 along a direction substantially parallel to a tangent at the point at which the brake arm end portion 99 engages the peripheral surface of the associated drive wheel. In this manner, the end portion 99 pivots upward and downward on a smaller and intersecting arc to that of the second associated drive wheel. In the activated position, the distal end portion 99 of the brake arm 94 prevents the first drive wheel 30a from rotating about a central axis thereof in a rearward direction, yet does not prevent the first drive wheel 30a from rotating about the central axis thereof in a forward direction.

When a patient attempts to rest into the seating area of the wheelchair 10, the weight of the patient imparts a downward force on the seat member 26, which causes the seat member 26 to flex, bend, slide, or otherwise move in a downward direction to its lower position. The downward movement of the seat member 26 translates the downward force to the actuator lever 75, thereby pivoting the actuator lever 76 downward as indicated by the arrow in FIG. 2A. As the actuator lever 76 pivots, the adjustor plate 78 is rotated about its longitudinal axis to translate a corresponding rotational movement to pivotable collar 54. As the collar 54 rotates about its axis, the brake arm 94 operatively associated therewith is pivoted about the region of its proximal end portion 96 accommodated in the second bore 70 so that the distal end portion 99 is moved substantially along the forward rotational direction from the activated position to a non-activated position. In the non-activated position, the distal end portion 99 is radially spaced from the drive wheel 30a and, hence, does not interfere with manual operation (including both forward and rearward motion) of the wheelchair 10.

Conversely, when an occupant of the wheelchair 10 attempts to rise from the seating area, the torsion spring 62 imparts a biasing force to urge the brake-arm supporting member 54 towards the first position, which in turn urges the seat member 26 towards its upper position and the distal end portion 99 of the brake arm 94 to move in a downward manner along an arcuate path (as shown by the arrow in FIG. 2B) that is, substantially along a rearward rotational direction into the activated position.

In the illustrated embodiment, the arcuate path that the distal end portion 99 of the brake arm 94 follows between the activated and non-activated positions intersects the circumference of the drive wheel 30a. Consequently, the amount of frictional force applied to the brake arm 94 by the drive-wheel 30a is proportional to the rearward force applied to the wheelchair 10. Stated differently, when the wheelchair 10 is moved rearwardly, frictional force between the drive wheel 30a and the brake arm 94 causes the distal end portion 99 of the brake arm 94 to move in a generally radially inward direction towards the hub 32a, which further presses the distal end portion 99 into the drive wheel 30a. Consequently, continued rearward motion of the wheelchair 10 has a corresponding immobilizing effect on the drive wheel 30a of the wheelchair 10.

Accordingly, even though the occupant of the wheelchair 10 may neglect to set a conventional parking brake (not shown), the chair 10 is automatically immobilized against backward movement by the anti-rollback device when the occupant is attempting to rise from or seat himself in the seat member 26.

Figure 6:
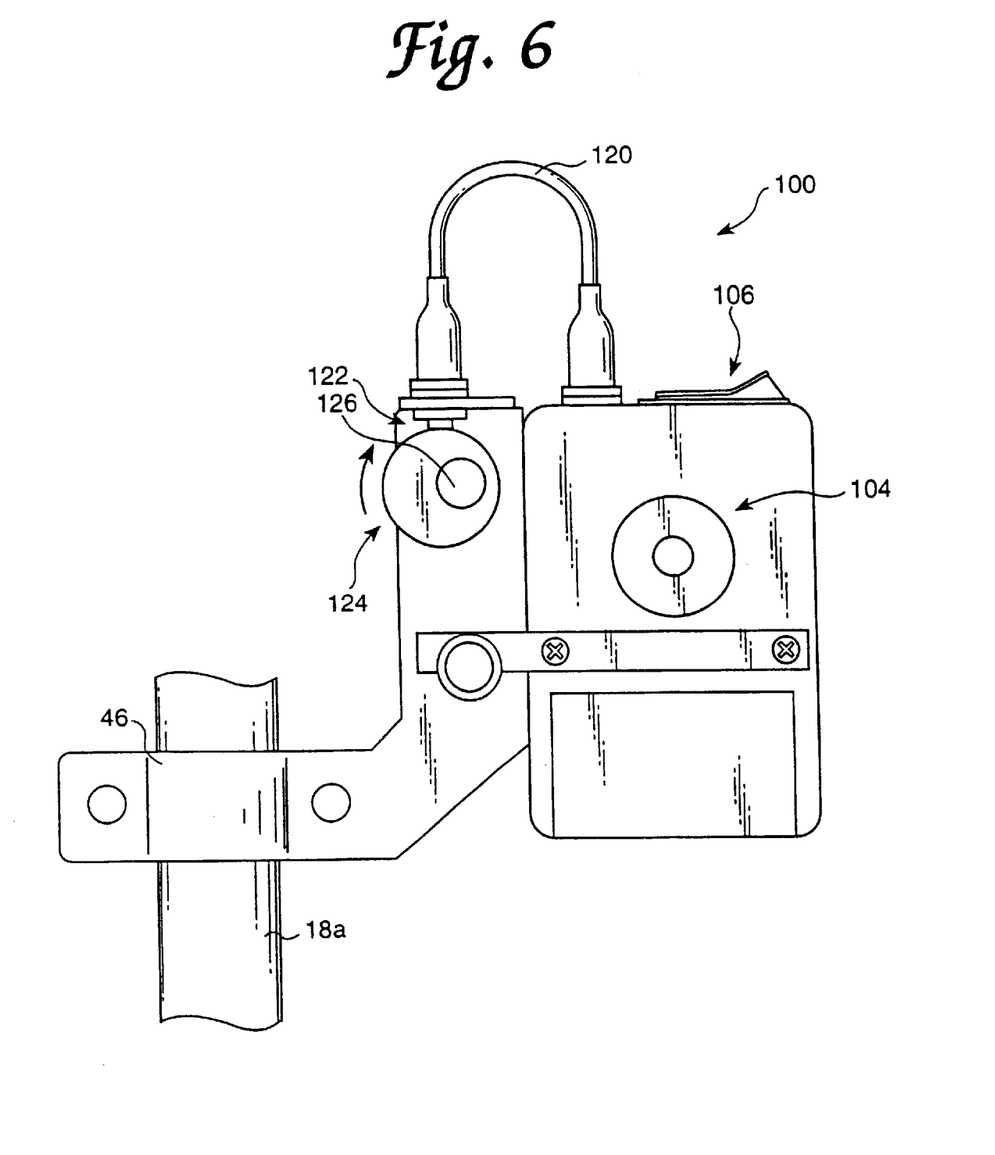
FIG. 6 is a side view of an ambulation monitor according to one embodiment of the present invention.
Figure 7:
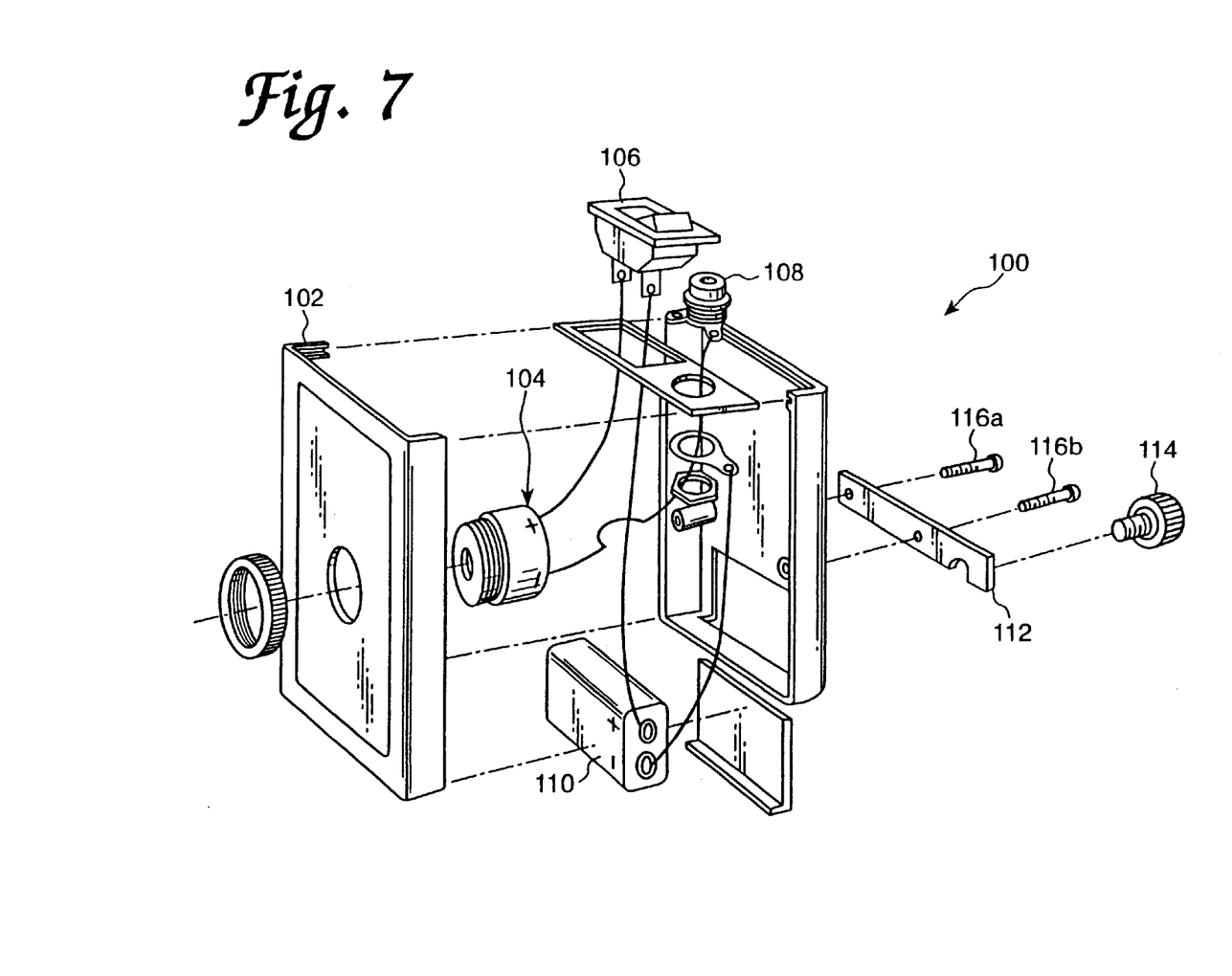
FIG. 7 is an exploded view of the ambulation monitor of FIG. 6.

Referring now to FIGS. 6 and 7, according to another embodiment of the present invention the wheelchair is equipped with an ambulation monitor, generally designated by reference numeral 100, for activating an alarm when the occupant of the wheelchair 10 attempts to rise from the seat member 26.

As shown in FIG. 7, the ambulation monitor includes a housing structure 102, which houses a horn 104, an on/off switch 106 and a switch jack 108 electrically connected to the horn 104, and an energy source 110, e.g., a battery, electrically connected to the on/off switch 106. The housing structure 102 is supported on the mounting bracket 44 with a mounting bracket 112, a mounting bracket clamp knob 114, and screws 116a and 116b.

Referring now to FIG. 6, a connector wire 120 electrically connects the switch jack 108 to a cam actuator switch 122. A cam 124 is cooperatively associated with the pivotable collar 54 by providing the cam 124 with an eccentrically disposed aperture 126 through which a portion of the pivotable collar 54 is disposed. Accordingly, when the occupant begins to rise from the seat member 26, the pivotable collar 54 is rotated about its longitudinal axis as described above. The cam 124, by virtue of its cooperative association with the pivotable collar 54, rotates to actuate the switch 122, thereby activating the horn 104 to alert staff of the occurrence.

In its broadest aspects, several variations and modifications to the above-discussed anti-rollback assembly can be implemented without departing from the scope of the present invention. For example, the anti-rollback assembly 40 may include a separate biasing member or members, such as springs, to urge the seat member into its upper position independent of or in conjunction with the torsion spring 62. Also, although in the illustrated embodiment each of the drive wheels 30a and 30b and a one-way brake assembly (that is, a mounting assembly and brake arm) associated therewith, it is understood that the anti-rollback assembly 40 may include only one mounting assembly 42 and brake arm 94, in which case, for example, a pivotable bar (not shown) may interconnect the brake releasing assembly 74 with the side frame 14b not associated with the mounting assembly 42 and brake arm 94. Where the anti-rollback assembly includes one-way brake assemblies respectively associated with each of the drive wheels 30a and 30b (as shown in FIGS. 1, 2A, and 2B), a second torsion spring (not shown) may be accommodated in the mounting bracket associated with the second drive wheel 30b; alternatively, the anti-rollback assembly 40 may include only a single torsion spring, since the pivotable collar 54 associated with the first drive wheel 30a rotates in unison with the pivotable collar associated with the second drive wheel 30b due to the interconnection provided by the brake releasing assembly 74.

The one-way brake assemblies may respectively engage portions of the rear drive wheel assemblies at positions other than the rear drive wheel. For example, although not shown, the assemblies could include ratchet and pawl wheel assemblies to accomplish the anti-rollback function of the present invention.

These and other modifications to the assembly, when viewed with reference to this disclosure, are within the purview of those skilled in the art.

If desired, the automatic anti-rollback assembly 40 of the present invention may be used in conjunction with conventional supplemental braking devices well known in the art, including, for example, a manually-operated parking brake to immobilize the wheelchair from forward or rearward movement when occupied.

This application claims priority of provisional patent application No. 60/039,485, the complete disclosure of which is incorporated herein by reference.

The foregoing detailed description of the preferred embodiments of the invention has been provided for the purposes of illustration and description. It is not intended to be exhaustive or to limit the invention to the precise embodiments disclosed. The embodiments were chosen and described in order to best explain the principles of the invention and its practical application, thereby enabling others skilled in the art to understand the invention. While the invention has been described in connection with what is presently considered to be the most practical and preferred embodiments, it is understood that the invention is not limited to the disclosed embodiments, but, on the contrary, is intended to cover various modifications and equivalent arrangements included within the spirit and scope of the appended claims.

What is claimed is:

1. A wheelchair comprising:

a frame structure;

a rear drive wheel assembly rotatably supported by said frame structure;

a front wheel assembly rotatably supported by said frame structure;

a seat member supported by said frame structure and constructed and oriented to accommodate an occupant;

a one-way brake assembly including a one-way brake member, said one-way brake-assembly being movable between a non-activated position in which said one-way brake member is positioned to permit said rear drive assembly to rotate in forward and rearward directions to enable said wheelchair to move freely in both the forward and rearward directions, and an activated position in which said one-way brake member is positioned to prevent rotation of said rear drive wheel assembly in the rearward direction so as to prevent movement of said wheelchair in the rearward direction while continuing to permit rotation of said rear drive wheel assembly in said forward direction for forward movement of said wheelchair;

a biasing member operatively associated with said one-way brake assembly to bias said one-way brake assembly towards the activated position; and a brake releasing assembly operatively associated with said one-way brake assembly and said biasing member, said brake releasing assembly being movable in response to said wheelchair being occupied to overcome the bias of said biasing member so as to move said one-way brake assembly from the activated position to the non-activated position, thus enabling said wheelchair to freely move in both the forward and rearward directions.

2. A wheelchair according to claim 1, wherein said rear drive wheel assembly includes first and second drive wheels, wherein said one-way brake member is disposed in surface engagement with said first and second drive wheels to prevent rearward movement of said wheelchair when said brake assembly is in the activated position, and wherein said one-way brake member is spaced from said first and second drive wheels when said brake assembly is in the non-activated position to permit said first and second drive wheels to rotate freely and thereby enable said wheelchair to move in the forward and rearward directions.

3. A wheelchair comprising:
a frame structure;
a rear drive wheel assembly comprising first and second drive wheels rotatably supported by said frame structure;
a front wheel assembly comprising first and second front wheels rotatably supported by said frame structure;
a seat member supported by said frame structure and constructed and oriented to accommodate an occupant;
first and second one-way brake assemblies, each of which includes a one-way brake member, said first and second one-way brake assemblies being movable between a non-activated position in which said one-way brake members are positioned to permit said rear drive wheel assembly to rotate in forward and rearward directions to enable said wheelchair to move freely in both the forward and rearward directions, and an activated position in which said one-way brake members are positioned to prevent rotation of said rear drive wheel assembly in the rearward direction so as to prevent movement of said wheelchair in the rearward direction while continuing to permit rotation of said rear drive wheel assembly in the forward direction for forward movement of said wheelchair;
a biasing member operatively associated with at least one of said one-way brake assemblies to bias said at least one of said one-way brake assemblies towards the activated position; and
a brake releasing assembly operatively associated with said biasing member and said at least one of said one-way brake assemblies, said brake releasing assembly being movable in response to said wheelchair being occupied to overcome the bias of said biasing member so as to move said at least one of said one-way brake assemblies from the activated position to the non-activated position, thus enabling said wheelchair to freely move in both the forward and rearward directions.

4. A wheelchair according to claim 3, wherein said first and second one-way brake members are respectively disposed in surface engagement with said first and second drive wheels to prevent rearward movement of said wheelchair when said brake assembly is in the activated position, and wherein said first and second one-way brake members are respectively spaced from said first and second drive wheels when said brake assembly is in the non-activated position to permit said first and second drive wheels to rotate freely and thereby enable said wheelchair to move in the forward and rearward directions.

5. A wheelchair according to claim 3, wherein said biasing member is operatively associated with both of said first and second one-way brake assemblies to bias said first and second one-way brake assemblies toward the activated position, and further wherein said brake releasing assembly is operatively associated with said biasing member and said first and second one-way brake assemblies, said brake releasing assembly being movable in response to said wheelchair being occupied to overcome the bias of said biasing member so as to move said first and second one-way brake assemblies from the activated position to the non-activated position, thus enabling said wheelchair to freely move in both the forward and rearward directions.

6. A wheelchair according to claim 5, wherein said seat member is movable from an upper position to a lower position in response to the weight of the occupant, and wherein said seat member is cooperatively associated with said brake releasing assembly to move said first and second one-way brake assemblies from the activated position to the non-activated position in response to downward movement of said seat member from the upper position to the lower position.

7. A wheelchair according to claim 6, wherein said seat member is biased towards the upper position by said biasing member.

8. A wheelchair according to claim 7, wherein said one-way brake members of said first and second one-way brake assemblies follow respective arcuate paths between the activated position and the non-activated position, the arcuate paths of the first and second one-way brake assemblies intersect rotational paths of said first and second drive wheels, respectively.

9. A wheelchair according to claim 3, wherein said biasing member is a torsion spring.

10. A wheelchair according to claim 3, wherein said wheelchair further comprises an ambulation monitor operatively associated with said one-way brake assembly or said brake releasing assembly to activate an alarm when the wheelchair occupant attempts to rise from said seat member.

11. An anti-rollback assembly comprising:
first and second one-way brake assemblies, each of said brake assemblies including a mounting assembly mountable on a frame structure of a wheel chair and a one-way brake member associated with and supported by said mounting assembly, each of said one-way brake members having a distal end portion movable along an arcuate path relative to said associated mounting assembly;
a brake releasing assembly operatively associated with said first and second one-way brake assemblies so as to move said one-way brake members of said one-way brake members of said one-way brake assemblies along the arcuate path;
wherein each of said first and second one-way brake assemblies includes a rotatable brake-member supporting member supporting said one-way brake member in such a manner that rotation of said brake-member supporting member about a longitudinal axis thereof moves said one-way brake member along the arcuate path;

wherein said brake releasing assembly comprises an actuating lever and adjustable length connecting plates operatively connecting said first and second one-way brake assemblies to said actuating lever.

12. A wheelchair comprising:

a frame structure;

a wheel assembly comprising a plurality of wheels for supporting said frame structure and being rotatable for enabling forward and rearward rolling movement of the wheelchair;

a seat member supported by said frame structure, and seat member being constructed and oriented to accommodate an occupant;

a one-way brake assembly comprising a one-way brake member, said one-way brake assembly being movable between (a) an activated position wherein said one-way brake member is positioned to prevent rolling movement of said wheelchair in the rearward direction while continuing to permit rolling movement of said wheelchair in said forward direction and (b) a non-activated position wherein said one-way brake member is positioned to permit rolling movement of said wheelchair in both the forward and rearward directions; and an occupant responsive brake release associated with said seat member and said one-way brake assembly, said brake release (a) being responsive to an occupant sitting upon said seat member to move said one-way brake assembly from the activated position to the non-activated position, thus responsively positioning said brake member to permit rolling movement of said wheel chair in both the forward and rearward directions and (b) being responsive to an occupant rising from said seat member to move said one-way brake assembly from the non-activated position to the activated position, thus responsively positioned said brake member to prevent rolling movement of said wheelchair in the rearward direction while continuing to permit forward rolling movement of said wheelchair.

13. A wheelchair according to claim 12, wherein said one-way brake assembly further comprises a biasing member that biases said one-way brake assembly to said activated position thereof, said brake release being responsive to an occupant sitting upon said seat member to move said one-way brake assembly from the activated position to the non-activated position against the biasing of said biasing member.

14. A wheelchair according to claim 13, wherein said biasing member is a torsion spring.

15. A wheelchair according to claim 12, wherein said brake member is a first brake member and wherein said one-way brake assembly further comprises a second brake member spaced laterally from said first brake member, said second brake member being movable along with said first brake member (a) so that both said first and second brake members are positioned to prevent rolling movement of said wheelchair in the rearward direction while continuing to permit forward rolling movement of said wheelchair in said activated position of said one-way brake assembly, and (b) so that both said first and second brake members are positioned to permit rolling movement of said wheelchair in both the forward and rearward directions.

16. A wheelchair according to claim 15, wherein said first and second brake members extend generally rearward with respect to said wheelchair and are moved downwardly as said one-way brake assembly moves from said non-activated position to said activated position.

17. A wheelchair according to claim 16, wherein said first and second brake members move along an arcuate path as said one-way brake assembly moves between said non-activated position and said activated position.

18. A wheelchair according to claim 17, wherein said seat member is movable from an upper position to a lower position in response to the weight of the occupant seating thereupon, and wherein said seat member is operatively associated with said brake release to move said one-way brake assembly from the activated position to the non-activated position in response to downward movement of said seat member from the upper position to the lower position.

19. A wheelchair according to claim 18, wherein said wheel assembly includes a rear wheel assembly and a front wheel assembly.

20. A wheelchair according to claim 19, wherein said rear drive wheel assembly includes first and second drive wheels, wherein said first and second brake members in the activated position of said one-way brake assembly engage said first and second drive wheels to prevent rotational movement of said rear drive wheels corresponding to rearward rolling movement of said wheelchair while continuing to permit rotational movement of said first and second drive wheels corresponding to forward rolling movement of said wheelchair, and wherein said first and second brake members in said non-activated position of said one-way brake assembly are spaced from said first and second drive wheels to permit said first and second drive wheels to rotate freely and thereby permit rolling movement of said wheelchair in the forward and rearward directions.

21. An anti-rollback assembly for installation on a wheelchair, the wheelchair comprising a frame structure; a wheel assembly comprising a plurality of wheels for supporting said frame structure and being rotatable for enabling forward and rearward rolling movement of the wheelchair; and a seat member supported by said frame structure, said seat member being constructed and oriented to accommodate an occupant; said anti-rollback assembly comprising:

a mounting structure constructed and arranged to mount said anti-rollback assembly on the frame structure of the wheelchair so that said anti-rollback assembly is installed in an operative position;

a one-way brake assembly comprising a one-way brake member, said one-way brake assembly being movable between (a) an activated position wherein, when said anti-rollback assembly is installed in the operative position, said one-way brake member is positioned to prevent rolling movement of said wheelchair in the rearward direction while continuing to permit rolling movement of said wheelchair in said forward direction (b) a non-activated position wherein, when said anti-rollback assembly is installed in the operative position, said one-way brake member is positioned to permit rolling movement of said wheelchair in both the forward and rearward directions; and an occupant responsive brake release associated with said seat member and said one-way brake assembly, said brake release when said anti-rollback assembly is installed in the operative position (a) being responsive to an occupant sitting upon said seat member to move said one-way brake assembly from the activated position to the non-activated position, thus responsively positioning said brake member to permit rolling movement of said wheelchair in both the forward and rearward directions and (b) being responsive to an occupant rising from said seat member to move said one-way brake assembly from the non-activated position to the activated position, thus responsively positioning said brake member to prevent rolling movement of said wheelchair in the rearward direction while continuing to permit forward rolling movement of said wheelchair.

22. An anti-rollback assembly according to claim 21, wherein said one-way brake assembly further comprises a biasing member that biases said one-way brake assembly to said activated position thereof, said brake release being responsive to an occupant sitting upon said seat member to move said one-way brake assembly from the activated position to the non-activated position against the biasing of said biasing member.

23. An anti-rollback assembly according to claim 22, wherein said biasing member is a torsion spring.

24. An anti-rollback assembly according to claim 21, wherein said brake member is a first brake member and wherein said one-way brake assembly further comprising a second brake member spaced laterally from said first brake member, said second brake member being movable along with said first brake member (a) so that both said first and second brake members are positioned to prevent rolling movement of said wheelchair in the rearward direction while continuing to permit forward rolling movement of said wheelchair in said activated position of said one-way brake assembly when said anti-rollback assembly is installed in said operative position, (b) so that both said first and second brake members are positioned to permit rolling movement of said wheelchair in both the forward and rearward directions when said anti-rollback assembly is installed in said operative position.

25. An anti-rollback assembly according to claim 24, wherein when said anti-rollback assembly is installed in said operative position said first and second brake members extend generally rearward with respect to said wheelchair and are moved downwardly as said one-way brake assembly moves from said non-activated position to said activated position.

26. An anti-rollback assembly according to claim 25, wherein when said anti-rollback assembly is installed in said operative position said first and second brake members move along an arcuate path as said one-way brake assembly moves between said non-activated position and said activated position.

27. An anti-rollback assembly according to claim 26, wherein when said anti-rollback assembly is installed in said operative position said brake release moves said one-way brake assembly from the activated position to the non-activated position in response to a downward movement of said seat member occurring due to the weight of the occupant seating thereupon.

28. An anti-rollback assembly according to claim 27, wherein when said anti-rollback assembly is installed in said operative position said first and second brake members in the activated position of said one-way brake assembly engage first and second rear drive wheels of the wheelchair to prevent rotational movement of the rear drive wheels corresponding to rearward rolling movement of said wheelchair while continuing to permit rotational movement of the rear drive wheels corresponding to forward rolling movement of said wheelchair, and wherein said first and second brake members in said non-activated position of said one-way brake assembly are spaced from the rear drive wheels to permit said rear drive wheels to rotate freely and thereby permit rolling movement of the wheelchair in the forward and rearward directions.

29. A method for preventing rollback of a wheelchair, the wheelchair comprising a frame structure; a wheel assembly comprising a plurality of wheels for supporting said frame structure and being rotatable for enabling forward and rearward rolling movement of the wheelchair; a seat member supported by said frame structure, said seat member being constructed and oriented to accommodate an occupant; and a one-way brake assembly comprising a one-way brake member, said one-way brake assembly being movable between (a) an activated position wherein said one-way brake member is positioned to prevent rolling movement of said wheelchair in the rearward direction while continuing to permit rolling movement of said wheelchair in said forward direction and (b) a non-activated position wherein said one-way brake member is positioned to permit rolling movement of said wheelchair in both the forward and rearward directions; said method comprising:

moving said one-way brake assembly, with an occupant responsive brake release associated with said seat member and said one-way brake assembly, from said non-activated position to said activated position in response to an occupant rising from said seat member, thus responsively positioning said brake member to prevent rolling movement of said wheelchair in the rearward direction while continuing to permit forward rolling movement of said wheelchair.

\* \* \* \* \*

(12) EX PARTE REEXAMINATION CERTIFICATE (4929th)
United States Patent
Richie et al.

(10) Number: US 6,371,503 C1
(45) Certificate Issued: *Apr. 20, 2004

(54) WHEELCHAIR AUTOMATIC ANTI-ROLLBACK ASSEMBLY

(75) Inventors: James K. Richie, Waterford, CT (US); James A. Marquis, Springfield, MA (US)

(73) Assignee: 210 Innovations LLC, Waterford, CT (US)

Reexamination Request:
No. 90/006,566, Mar. 14, 2003

Reexamination Certificate for:
Patent No.: 6,371,503
Issued: Apr. 16, 2002
Appl. No.: 09/910,737
Filed: Jul. 24, 2001

( * ) Notice: This patent is subject to a terminal disclaimer.

Related U.S. Application Data (63) Continuation of application No. 09/578,488, filed on May 26, 2000, now Pat. No. 6,279,936, which is a continuation of application No. 09/026,902, filed on Feb. 20, 1998, now Pat. No. 6,092,824.
(60) Provisional application No. 60/039,485, filed on Feb. 28, 1997.

(51) Int. Cl.[7] .............................................. B62M 1/14
(52) U.S. Cl. ............................... 280/304.1; 280/250.1; 188/2 F (56) References Cited

U.S. PATENT DOCUMENTS

| | | | |
|---|---|---|---|
| 196,570 A | | 10/1877 | Dyer |
| 633,266 A | | 9/1899 | Jamieson |
| 1,090,011 A | | 3/1914 | Ballinger |
| 2,259,924 A | | 10/1941 | Connolly |
| 2,753,919 A | | 7/1956 | Sill |
| 2,765,839 A | | 10/1956 | Arpin |
| 2,792,874 A | | 5/1957 | Sundberg |
| 3,302,757 A | * | 2/1967 | Eagleson, Jr. et al. |
| 3,529,700 A | * | 9/1970 | Marshall |
| 3,903,513 A | * | 9/1975 | Green et al. ................. 340/278 |
| 4,033,433 A | | 7/1977 | Kirk |
| 4,320,818 A | | 3/1982 | Knoche |
| 4,476,964 A | | 10/1984 | Broman |
| 4,538,825 A | * | 9/1985 | Delahoussaye et al. ................... 280/242 WC |
| 4,560,033 A | * | 12/1985 | DeWoody et al. .......... 188/2 F |
| 4,565,385 A | | 1/1986 | Morford |
| 4,623,043 A | * | 11/1986 | Babilas ....................... 188/2 F |
| 4,691,933 A | | 9/1987 | Strauss |
| 4,877,260 A | | 10/1989 | Howland |
| 4,887,830 A | * | 12/1989 | Fought et al. ........... 280/304.1 |
| 5,137,295 A | | 8/1992 | Peek |
| 5,197,750 A | * | 3/1993 | DiGeorge ................ 280/250.1 |
| 5,203,433 A | * | 4/1993 | Dugas ........................ 188/2 F |
| 5,232,236 A | | 8/1993 | Korpi |
| 5,358,266 A | | 10/1994 | Roth et al. |
| 5,577,748 A | | 11/1996 | Dombrowski et al. |
| 5,984,334 A | | 11/1999 | Dugas |

FOREIGN PATENT DOCUMENTS

| | | |
|---|---|---|
| GB | 2 034 427 A | 6/1980 |
| WO | 90/14064 | 11/1990 |
| WO | WO90/14064 | 11/1990 |
| WO | 90/14065 | 11/1990 |

* cited by examiner

*Primary Examiner*—Kevin Hurley (57) ABSTRACT

An anti-rollback assembly adapted or adaptable for use in combination with a wheelchair. The anti-rollback assembly includes a one-way brake assembly automatically immobilizing the wheelchair against rearward movement when the occupant attempts to rise from or sit in a seat member of the wheelchair, yet at the same time does not prevent the wheelchair from moving in a forward direction. Conversely, when the occupant is fully seated in the seat member, the one-way brake assembly is disengaged so that the wheelchair can move freely in forward or rearward directions. The assembly can be retrofitted onto existing wheelchairs, and is adjustable to fit various size wheelchairs.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–29 is confirmed.

\* \* \* \* \*